United States Patent
Azizian et al.

(10) Patent No.: US 7,711,411 B2
(45) Date of Patent: May 4, 2010

(54) METHOD OF IN-VIVO MEASUREMENT OF FAT CONTENT OF A BODY AND APPARATUS THEREFOR

(75) Inventors: Hormoz Azizian, Mississauga (CA); Suzanna Winsborough, Mississauga (CA); Michael Younikian, Mississauga (CA); Carolyn Winsborough, Mississauga (CA)

(73) Assignee: NIR Technologies Inc., Oakville, Ontario (CA)

( * ) Notice: Subject to any disclaimer, the term of this patent is extended or adjusted under 35 U.S.C. 154(b) by 1010 days.

(21) Appl. No.: 10/293,766

(22) Filed: Nov. 13, 2002

(65) Prior Publication Data

US 2004/0092803 A1 May 13, 2004

(51) Int. Cl.
*A61B 6/00* (2006.01)

(52) U.S. Cl. .................. 600/474; 600/310; 600/473; 600/476; 250/339.02

(58) Field of Classification Search ............... 600/474, 600/473, 310, 476; 250/339.02
See application file for complete search history.

(56) References Cited

U.S. PATENT DOCUMENTS

| | | | |
|---|---|---|---|
| 4,798,955 A | | 1/1989 | Rosenthal |
| 4,801,804 A | | 1/1989 | Rosenthal |
| 4,850,365 A | * | 7/1989 | Rosenthal .................. 600/473 |
| 4,895,163 A | | 1/1990 | Libke et al. |
| 4,928,014 A | * | 5/1990 | Rosenthal ............... 250/341.5 |
| 4,990,772 A | * | 2/1991 | Rosenthal ............... 250/252.1 |
| 5,105,825 A | | 4/1992 | Dempster |
| 5,377,003 A | * | 12/1994 | Lewis et al. ................ 356/300 |
| 5,440,388 A | | 8/1995 | Erickson |
| 5,991,028 A | * | 11/1999 | Cabib et al. ................ 356/456 |
| 6,014,222 A | | 1/2000 | Borggaard et al. |
| 6,336,044 B1 | | 1/2002 | Ghiassi et al. |
| 6,353,471 B1 | | 3/2002 | Samsoondar et al. |

(Continued)

FOREIGN PATENT DOCUMENTS

CA    2183085    *    8/1995

(Continued)

OTHER PUBLICATIONS

W. Herres and J. Gronholz, Understanding FT-IR Data Processing, Part 1: Data Acquisition and Fourier Transformation, Comp. Appl. Lab. 4(1984), 216, pp. 1-5.

(Continued)

*Primary Examiner*—Brian Casler
*Assistant Examiner*—James Kish
(74) *Attorney, Agent, or Firm*—Gerald A. Gowan; Gowan Intellectual Property

(57) ABSTRACT

A method of in-vivo fat measurement of humans or animals by scanning the ear of the subject using a fibre optic probe delivering a light beam of Near infrared wavelengths provided by a NIR source. Passing the beam through an interferometer to encode data from the whole spectral range simultaneously. Detecting reflected light by a detector and applying Fourier Transform techniques to determine the intensity of the light in at least one narrow wave band selected for its correspondence to a form of fat. Recording the NIR response and determining the fat content of the body by either comparison to known reference samples or by use of an empirical formula.

10 Claims, 7 Drawing Sheets

U.S. PATENT DOCUMENTS

| | | | | |
|---|---|---|---|---|
| 6,475,800 | B1* | 11/2002 | Hazen et al. | 436/8 |
| 6,493,566 | B1* | 12/2002 | Ruchti et al. | 600/310 |
| 6,501,982 | B1* | 12/2002 | Ruchti et al. | 600/473 |
| 6,587,702 | B1* | 7/2003 | Ruchti et al. | 600/310 |
| 6,690,996 | B2* | 2/2004 | Seiler | 700/228 |
| 6,697,665 | B1* | 2/2004 | Rava et al. | 600/475 |
| 6,865,408 | B1* | 3/2005 | Abbink et al. | 600/310 |
| 2002/0010400 | A1* | 1/2002 | Camacho et al. | 600/473 |
| 2003/0071216 | A1* | 4/2003 | Rabolt et al. | 250/339.02 |
| 2003/0176808 | A1* | 9/2003 | Masuo | 600/547 |

FOREIGN PATENT DOCUMENTS

| | | | |
|---|---|---|---|
| CA | 2397611 | | 7/2001 |
| CA | 2397611 | * | 7/2005 |

OTHER PUBLICATIONS

J. Gronholz and W. Herres, Understanding FT-IR Data Processing, Part 2: Details of the Spectrum Calculation, Instruments & Computers 3 (1985), 10, pp. 6-12.

Joern Gronholz and Werner Herres, Understanding FT-IR Data Processing, Part 3: Further Useful Computational Methods, , pp. 13-23.

Joan M. Conway, Karl H. Norris, and CE Bodwell, A new approach for the estimation of body composition . . . , The American Journal of Clinical Nut . . . 40:Dec. 1984 pp. 1123-1130, USA.

Kathleen Martin, Depth-profiling of skin by near-infrared spectroscopy in *Near-infrared Spectroscopy: The future waves*, p. 328.

Vu, Thanh. *Standardization of body surface area calculation.* From www.halls.md/bsa/bsa VuReort.htm.

Gehan, Edmund A., George, Stephen L. Estimation of human Body Surface Area From Height and Weight. *Cancer Chemother rep* 54 :228, 1970.

Ross, Robert. Magnetic resonanace imaging provides new insights into the characterization of adipose and lean tissue distribution . *Can. Jo. Physio. Pharmacol.* 74: 778-785 (1996).

Sohlstroem, Annica, et al. Adipose tissue distribution as assessed by magnetic resonance imaging and total body fat by magnetic resonance imaging, underwater weighting, and body-water dilution in healthy women. *Am J Clin Nutr* 1993; 58 ;830-8.

Abate, Nicola, et al. Estimation of adipose tisse mass by magnetic resonanace imaging: validation agaist dissection in human cadavers. *Journal of Lipid Research,* vol. 35, 1994.

Staten, M.A., et al. Measurement of Fat Distribution by Magnetic Resonance Imaging. *Investigative Radiology,* vol. 2 (May 1989).

Schreiner, Pamela J. Sex specific Associations of Magnetic resonance Imaging-derived Intr-abdominal and Subcutaneous Fat areas with Conventional Anthropometric Indices. *American Journal of Epidemiology,* vol. 144, No. 4 (1996).

Griffiths, Peter R., Fourier Transform Infrared Spectrometry. *Science,* vol. 222, Oct. 21, 1983, p. 297.

Ferraro, John R., Basile, Louis J., *Fourier Transform Infrared Spectroscopy* in Fourier Tranform Infrared Spectroscopy, Applications to Chemical Systems, p. 18-27.

"Periodic health examination, 1999 update; Detection, prevention and treatment of obesity", Douketis et al., CMAJ, Feb. 23, 1999; 160(4) at p. 513.

"Applied Body Composition Assessment, Second Edition"; Vivian H. Heyward and Dale R. Wagner; 2004.

"A Comparison of Methods to Determine Body Fat in Individuals wiht Cystic Fibrosis; A Pilot Study", Journal of Exercise Physiologyonline, vol. 6 No. 2 May 2003; Swisher et al.

"Near Infrared Spectroscopy; Fundamentals, Practical Aspects and Analytical Applications", J. Braz. Chem. Soc., vol. 14, No. 2, 198-219, 2003; Cello Pasquini.

* cited by examiner

METHOD OF IN-VIVO MEASUREMENT OF FAT CONTENT OF A BODY AND APPARATUS THEREFOR

FIELD OF THE INVENTION

The invention relates to a method for the in-vivo measurement of fat content of a body, such as a human or an animal, by the use of light in the near infrared region of the light spectrum, and the apparatus for measurement of body fat.

BACKGROUND OF THE INVENTION

Measurement of body fat in humans is one of the factors in checking the fitness and general health level of humans. Excess fat is known to be a risk factor with regard to heart disease, diabetes, and even cancer of certain kinds. Excess fat has recently come under a high degree of scrutiny by the health industry, and it is desirable to be able to make an accurate measurement of body fat in order to assess health risks.

Obesity is currently defined by a "body mass index" or BMI. A BMI of more than 27, according to Health Canada guidelines, is regarded as obese. However, recent reports suggest that the use of the BMI alone leads to two common forms of misclassification. The first is of a highly muscular individual with a high BMI who may be classified as "overfat", when, in fact he/she is not. The second is of individuals with a healthy BMI (18.5 to 24.9) who actually do have an elevated body fat content and are at risk.

Another method for classifying body fat content is the density measurement. The percent body fat is calculated by an equation based on the density of the body. The density of the body is calculated by an equation that involves measuring a person suspended on a trapeze in the air, and then weighing the same person under water.

The equipment used for this measurement includes a special weigh scale, and a submersion pool or tank. Some of the drawbacks of this system are that the standard body density used for comparison is that of a young Caucasian. Modifications in the equations may be necessary for persons of other ethnic origins. In addition, some people feel uncomfortable when they must be fully submerged, leading to incorrect readings, the procedure requires a trained operator, and there is always air left in the lungs, and it is difficult to correct for this residual air accurately.

To date the usual and the cheapest method of fat measurement is conducted by a pair of calipers. The ends of the calipers are simply squeezed against a fold of the skin, at certain selected locations on the body. This system gives variable and erratic results, and is known to be unsatisfactory.

Systems for measurement of body fat have been proposed using near infrared light. One such proposal is described in experimental form in "A New Approach for the Estimation of Body Composition: Infrared Interactance", by Conway J et al, American Journal of Clinical Nutrition 40: December 1984, pages 1123 to 1130. Systems have been proposed in patent literature using near infrared light. One such system is described in U.S. Pat. No. 4,928,014, R D Rosenthal, dated May 22, 1990.

This system was later found to be unsatisfactory and unreliable.

Another system for the measurement of body fat is the system known as magnetic resonance imaging (MRI). This system provides much more accurate results than any other system known, at present. However, the equipment is a major investment, in the order of millions of dollars. The operation of it requires a highly trained team of medical assistants. The entire system takes a relatively long time to scan a person. As a result the per person costs of MRI are too high to enable it to be used simply for body fat measurement.

Another system is the Deuterium Oxide Dilution system, but this is also a technical and demanding system, and is not satisfactory for use in every day medical practice, or in fitness testing.

However, when a doctor is carrying out a physical exam of a person, which may be required for insurance, or for admission to certain types of employment, or which may be required by the individual for an annual monitoring of health, some form of measurement of fat content is usually carried out, as part of the overall tests used to evaluate the state of health of the individual.

Consequently, even though it is well known to be inaccurate, the standard test for evaluating the fat content of the human body has, for many years, been the skin fold caliper test.

There are three distinct categories for human fat. These are structural, metabolic and storage fats. Structural fats form part of each and every cell of the body, mainly in the cell membrane. Metabolic fats are a group of lipids that are used in metabolic processes. Storage fats represent the largest component of human fat. Part of the storage fat is found in the subcutaneous layer of the skin which is the third layer of skin found beneath the epidermis and dermis layers. The remaining smaller part of storage fat is used as a cushion for the visceral organs (liver, heart, kidneys, etc.).

There are several different types of fat found in the human body. Some occur naturally, others are only attainable by diet. Briefly, the types of fat are saturated fats, unsaturated fats, phospholipids and triglycerides.

Saturated fats are commonly found in animal fat products such as butter, lard and animal meats. Unsaturated fats, are divided into two groups, mono or poly unsaturated fats. An example of a monounsaturated fat is Oleic acid and can be found in olive oil. Polyunsaturated fats are essential fatty acids and are only attainable through diet. Examples of polyunsaturated fats are linoleic acid, linolenic and arachidonic acids. These are essential fatty acids and may be found in soy bean oil, peanut oil and corn oil to name a few.

Phospholipid, the most common of which is lecithin, is an important common component of all cell membranes.

Triglycerides, composed of three fatty acids attached to glycerol molecule and are the storage form of fat that occurs when humans eat calories in excess of their energy needs.

In the case of cattle carcasses, fat content has been measured in the carcass of the dead animal using a needle probe inserted into the carcass. This system has given satisfactory results. However, it is of use only after the animal has been slaughtered. Clearly it is of no use to humans. Even for animals, it gave a reading which was after the fact. By the time the measurement was available, it was then too late to make any attempt to correct the fat content of the animal by altering the diet. Fat content of animal carcasses is a major factor in the price for the carcasses received by the farmer. Market considerations require the carcass to have a low fat content. If the fat content is excessive then the farmer will receive less for the animals than if the fat content is lower.

Where animals are being raised for slaughter it would be preferable to be able to monitor the fat content of the animals in-vivo as they were being raised. If testing were available in-vivo the animals diet could be adjusted to maintain a desirable low fat content. However measurement of animal fat content, while the animal is alive, cannot be done with the invasive, needle probe type of measurement system.

Near Infrared (NIR) Spectroscopy, with its non-invasive, in-vivo capabilities can solve this problem. It is useful in examining aqueous solutions and mixtures, as well as biological studies. The interest in near infrared spectroscopy, for the analysis of chemicals, stems from a number of factors. Absorptions in the near infrared region arise from vibrational transitions to the second or higher energy states. Because of the very low probability of such transitions, absorption intensities are several orders of magnitude below those of the corresponding fundamental vibrations in the infrared and/or ultraviolet (UV) region of optical spectrum. Consequently infrared is not as sensitive in analysis of species present at low concentrations. Additionally, near infrared spectroscopy has the advantage that aqueous solutions can be readily analyzed without much interference from water absorption.

The intense absorption of near infrared wavelengths, by a species, also allows them to penetrate a sample sufficiently to be useful in the analysis of thicker samples, such as body tissue.

The use of light in the near infrared region of light spectrum for purposes of analysing for certain chemicals or for creating "images" is discussed in U.S. Pat. No. 5,440,388, R Erickson, dated Aug. 8, 1995. In this patent, there are descriptions of numerous different types of technology, all of which are mentioned incidentally, in passing. The actual invention described relates to a piece of equipment in which there are a plurality of discrete light sources each producing monochromatic light of a specific wavelength, the light sources being combined into a single beam of light. An interferometer modulates the light beam and a detector detects each of the discrete wavelengths. This is different than using Fourier Transform Near Infrared (FT-NIR) Spectroscopy. The FT-NIR instrument makes use of an interferometer to encode data from the whole spectral range simultaneously. The Michelson interferometer is used to produce a signal of a lower frequency than the frequency emitted from the NIR source. The lower frequency contains the same information as the original radiation signal, but is converted to a speed slow enough for detection by a detector. The output of the interferometer is an interferogram of all wavelengths emitted by the source. A computer then performs the Fast Fourier Transform of the interferogram and results in a frequency domain trace.

Fourier Transform Near Infrared Spectroscopy has certain advantages over traditional spectroscopy, in which the response of a sample to light is measured by scanning sequentially over a range of wavelengths. Fourier Transform Near Infrared Spectroscopy measures the response of the sample to all the wavelengths of interest simultaneously, by measuring the light after it interacts with the sample and recording the entire spectrum at once.

In the description of '388, it is stated that for various different samples, the light sources will have to be changed and the detectors will also have to be changed. This system is an array of light sources of specific wavelengths and an array of detectors for detecting such wavelengths. The system must therefore be specified for the particular chemical being analysed, or the nature of the specific sample being imaged.

The system described in '388 is not suitable for measurement of body fat because it does not provide any details on its resolution or accuracy or its ability for chemical analysis. This is different than using FT-NIR spectroscopy. The FT-NIR spectrometer, which, by contrast, makes use of an interferometer to encode data from the whole spectral range simultaneously. The description of '388 is focussed on imaging rather than chemical composition of the material. There is one statement in the description of '388 which appears to be inaccurate, where it speaks of;

"Near infrared spectroscopy was applied to human skin in the 1950's, and has since been developed for transcutaneous measurements of body fat composition."

There is no reference in the description for this assertion. In spite of a careful search of the literature, no such reference can be found.

It is desirable to provide a method of measurement of fat content of a body, whether human or animal, which is simple, accurate, and economical and which is non-invasive, and can be carried out in-vivo quickly, with lower cost equipment and with a minimum of training.

BRIEF SUMMARY OF THE INVENTION

With a view to providing a system for the in-vivo measurement of fat content of a body, the invention provides a method of in-vivo measurement of the fat content of a body containing at least one form of fatty acid having a reflectance characteristic corresponding to a narrow wave band of light in the near-infrared region of the spectrum, comprising the steps of providing a NIR-source emitting a laser light beam of near infrared intensity and passing said beam through an interferometer to encode data from the whole spectral range simultaneously; applying the near infrared beam through a fibre optic probe to a selected portion of the body having a relatively thin skin layer over a layer of cartilage; directing the reflected light beam from the skin to a detector; and next analysing the reflected light by Fourier Transform techniques to determine the intensity of light in at least one narrow wave band selected for its correspondence to a form of fat. In the preferred embodiment, the intensity of the reflected light is compared in that wave band with the reflective characteristics of reference materials with known fat content in said wave band, and thereby evaluating the fat content of the body.

In another embodiment, the second fat content measurement involves quantitative measurements using the physical parameters of height, weight and age of the subjects, along with the NIR response in an empirical equation to determine the total body fat content of humans.

The various features of novelty which characterize the invention are pointed out with more particularity in the claims annexed to and forming a part of this disclosure. For a better understanding of the invention, its operating advantages and specific objects attained by its use, reference should be made to the accompanying drawings and descriptive matter in which there are illustrated and described preferred embodiments of the invention.

DETAILED DESCRIPTION OF THE PREFERRED EMBODIMENT

The invention provides a method for determining the total fat content of the body using Fourier Transform Near infrared (FT-NIR) spectrometer and various calculations.

The present invention illustrated herein is a method of scanning and evaluating total body fat content in humans using non-invasive and in-vivo FT-NIR spectroscopy. Although the following outlines testing for humans, modifications may be made for testing of animals and fat content in animals.

The FT-NIR spectroscopy has a much higher resolution and accuracy level than Near Infrared (NIR) spectrometers. The FT-NIR spectrometer has a spectral resolution of 0.3 nm (2 cm$^{-1}$ at 8000 cm$^{-1}$) whereas other grating or filter instruments are between 2 nm (5 cm$^{-1}$ at 5000 cm$^{-1}$) to 10 nm (25 cm$^{-1}$ at 5000 cm$^{-1}$).

Dispersive instruments operate in a frequency domain whereas the Fourier Transformed NIR Infrared (FT-NIR) may be operated in the frequency domain or a time domain. The advantage of operating in a time domain allows for faster results.

Near infrared wavelengths of light are absorbed by species due to distinctive molecular vibrations and low level electronic excitations. Many molecules, particularly molecules of biochemical interest, have characteristic "fingerprint" absorption spectra in the near infrared.

The sample is placed adjacent to the output of the interferometer and the detector. The sample absorbs radiation of specific wave lengths. The unabsorbed radiation is reflected back to the detector and recorded as an interferogram. The interferogram is then transformed into a single channel spectrum by Fourier Transformation. The background spectrum is then used to calculate the transmission or absorption of the sample.

After an interferogram has been collected, a computer performs a Fast Fourier Transform (FFT), which results in a frequency domain trace (i.e. intensity vs wavenumber). The detector used in an FT-NIR instrument must respond quickly because intensity changes are rapid (the moving mirror moves quickly). To achieve a good signal to noise ratio, many interferograms are obtained and then averaged. This can be done in less time than it would take a dispersive instrument to record one scan.

Advantages of the Fourier Transform Near Infrared Spectrometers over Dispersive Near Infrared Spectrometers include:

Improved frequency resolution;
Improved frequency reproduceablity;
Higher energy throughput;
Faster operation computer based (allowing storage of spectra facilities for processing spectra)
Easily adapted for remote use.

Scanning of the different types of fats found in subcutaneous layer of skin using FT-NIR Spectroscopy and taking the second derivative of the spectra shows different spectral characteristics for the fatty acids or their combination.

Figure 1:
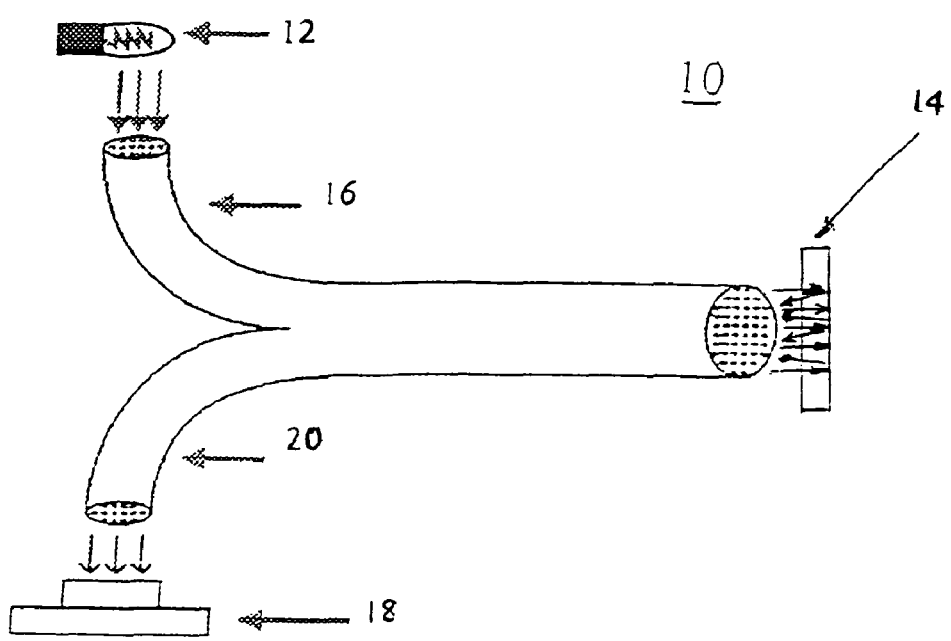
FIG. 1 illustrates a schematic of a fibre optic probe.
Figure 3:
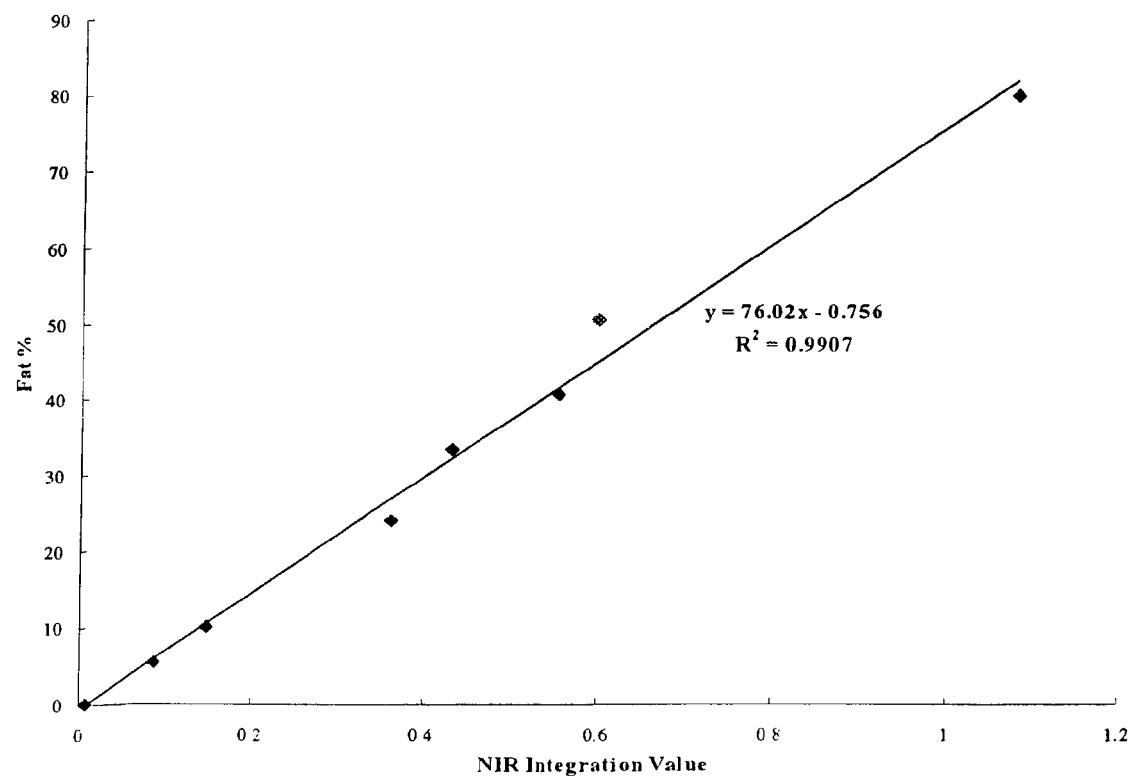
FIG. 3 illustrates a calibration curve of the NIR responses of reference samples plotted against the known percent fat content of the references.

Development of reference samples that contain a matrix that simulates the chemical composition of human tissue and containing known amounts of fatty acids are a significant factor in determining the in-vivo fat content of a human. The reference samples are developed and scanned using a Fibre Optic Probe (10), as illustrated in FIG. 1. As illustrated in FIG. 1, the Infrared source (12) emits a laser light beam of Near Infrared Radiation (NIR), which is delivered to the test sample (14) via a delivery fibre optic bundle (16). The NIR penetrates the sample (14) and specific wavelengths are absorbed or reflected. The reflected wavelengths are transmitted to a detector (18) via a collection fibre optic bundle (20). The reflected NIR wavelengths are recorded as an interferogram. The interferogram is then converted into a spectral reading, integrated, and the resulting data plotted against known fat content of the reference samples to create a calibration curve as shown in FIG. 3.

Figure 2:
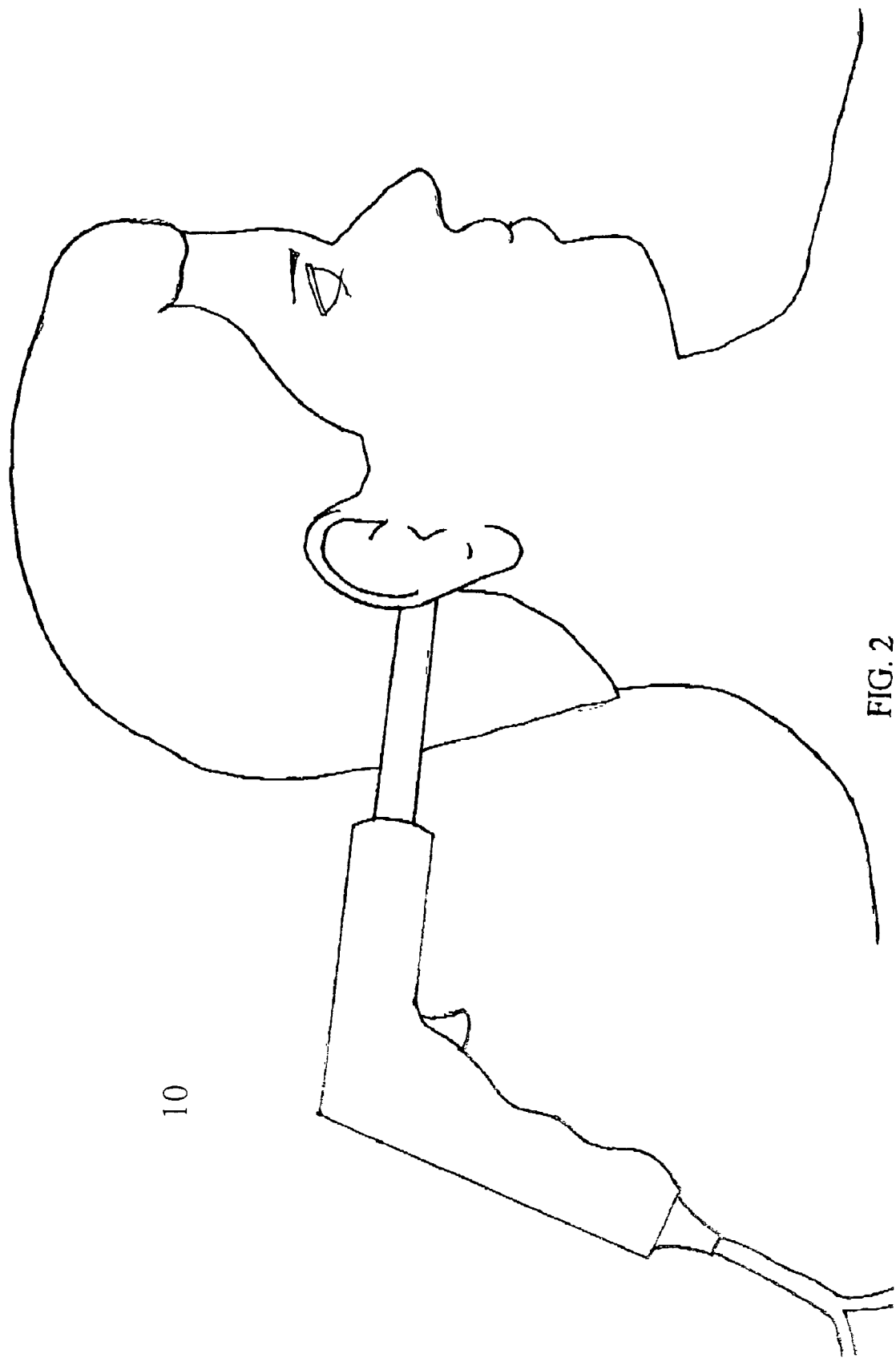
FIG. 2 illustrates the positioning of the fibre optic probe for scanning of the subject.

The methodology used to scan and determine fat content of a human is preferably as follows:

Fourier Transform Near Infrared Spectrometer probe (10) is used to scan the back of ear so that the laser is pointed away from eyes. This is best illustrated in FIG. 2;

measurements are taken, and as an example, each measurement may consist of five scans for a total of less than one minute;

dependent upon the results, the above step may be repeated;

following the scanning, data analysis is performed and the fat content is determined and recorded.

Although other parts of the body may be tested for fat content, scans of the ear, as shown in FIG. 2, were found to provide the most accurate readings when the results were compared to MRI readings. The ear is convenient, exposed, and has a thin layer of skin over cartilage, rendering the method of the invention convenient, safe and accurate.

Two different methods to determine the fat content can then be used. In the preferred embodiment, the NIR response, which is directly related to subcutaneous fat content of humans is matched to that of reference using the calibration curve (FIG. 3). In this embodiment standard reference samples are created having known concentrations of fat. The reference samples are scanned using the FT-NIR spectrometer. The results are then plotted against the known concentration of the reference sample producing the calibration curve of FIG. 3. The linear equation y=76.02x−0.756 is used to determine the subcutaneous fat content of humans where y would be the fat content in percent and x would be the total of the averages of the integration values at different frequencies.

Another embodiment involves integrating the NIR response of humans into an empirical equation (Table 2) taking gender, height, weight, and age into consideration. Both methods have been compared to MRI results to validate accuracy.

The following Table 1 displays the data for eighteen volunteers between the ages of 19 to 49.

TABLE 1

Volunteer Data

| ID No. | Gender | Height | Weight | Circ. (cm) | NIR Response | BMI | Fat % by Circumference[1] | NIR Fat % (Subcutaneous) |
|---|---|---|---|---|---|---|---|---|
| 1001 | M | 1.74 | 79.1 | 97 | 0.26 | 26 | 21.8 | 18.74 |
| 1002 | F | 1.65 | 61.4 | — | 0.46 | 23 | — | 33.30 |
| 1003 | M | 1.73 | 82.5 | 100 | 0.29 | 28 | 23.7 | 20.63 |
| 1004 | M | 1.75 | 61.4 | 77 | 0.15 | 20 | 9.4 | 10.20 |
| 1005 | M | 1.83 | 79.5 | 83 | 0.14 | 24 | 13.0 | 9.23 |
| 1006 | F | 1.63 | 67.3 | — | 0.38 | 25 | — | 27.34 |
| 1007 | M | 1.88 | 93.0 | 90 | 0.07 | 26 | 17.4 | 4.24 |
| 1008 | M | 1.74 | 84.1 | 94 | 0.29 | 28 | 19.9 | 20.63 |
| 1009 | F | 1.63 | 72.0 | — | 0.26 | 27 | — | 18.40 |
| 1010 | M | 1.91 | 95.0 | 91 | 0.28 | 26 | 17.7 | 19.89 |
| 1011 | F | 1.56 | 60.5 | — | 0.35 | 25 | — | 25.10 |
| 1012 | M | 1.83 | 79.5 | 83 | 0.24 | 24 | 13 | 16.91 |
| 1014 | M | 1.85 | 90.0 | 102 | 0.23 | 26.3 | 24.9 | 16.24 |
| 1015 | F | 1.58 | 54.5 | — | 0.43 | 22.0 | — | 31.21 |
| 1016 | F | 1.65 | 72.7 | — | 0.36 | 26.7 | — | 26.10 |
| 1017 | M | 1.83 | 68.0 | 80 | 0.14 | 20.3 | 11.2 | 9.57 |
| 1018 | M | 1.70 | 63.6 | 79 | 0.20 | 22.0 | 10.6 | 13.85 |
| 1019 | M | 1.78 | 95.4 | 95 | 0.31 | 30.1 | 20.6 | 22.25 |

Subject 1007 and 1010 show a similar weight and height with a similar abdominal circumference and have the same BMI. However, according to the NIR fat content measurement, subject 1007 (a body builder) has 15% less fat than subject 1010 (an average male). These results show that BMI can be misleading predictor of human health.

In the second embodiment an empirical equation is developed to determine the fat of humans. A certain percentage of fat is distributed subcutaneously throughout the human body and an empirical formula calculating the body surface area has been developed. By taking the height and weight of the subject, the NIR responses and the ratios of subcutaneous fat to total fat of each gender and age, the volume of subcutaneous fat can be determined and then converted to total fat content.

The original equation to determine body surface area of humans was formulated in 1916 by Dubois and Dubois based on 9 subjects. Since then, several updated formulas have become available. The Gehan and George formula was chosen for this analysis of body fat content as it is a more accurate version of the Mostellar formula, which is widely used across Canada as a standard at hospitals and clinics, and was based on the direct measurement of 401 individuals as compared to the Boyd formula which was based on 197 observations.

An empirical equation was developed using the NIR response, body surface area, fat density in humans, gender, age, and ratio of subcutaneous to total fat content obtained from MRI studies.

The empirical equation for total fat for each gender is shown below in Table 2.

EXAMPLES

1. Given: Gender=Male Age=49
Height=174 cm Weight=77.3 kg
NIR Response=0.29

$$TBF = \frac{64.719N * W^{0.51456} * H^{0.42246}}{(-0.003A + 0.9971)W}$$

$$= \frac{64.719(0.29) * (77.3)^{0.51456} * (174)^{0.42246}}{[-0.003(49) + 0.9971](77.3)}$$

$$= \frac{18.76851 * 9.366592802 * 8.841835596}{65.71273}$$

$$= 23.7\%$$

2. Given: Gender=Female Age=21
Height=163 cm Weight=67.3 kg
NIR Response=0.38

$$TBF = \frac{64.719N * W^{0.51456} * H^{0.42246}}{(-0.001A + 0.989)W}$$

$$= \frac{64.719(0.38) * (67.3)^{0.51456} * (163)^{0.42246}}{[-0.001(21) + 0.989](67.3)}$$

$$= \frac{24.59322 * 8.722147594 * 8.601234245}{65.1464}$$

$$= 28.3\%$$

TABLE 2

NIR Empirical Equation for total body fat.

| Females | Males |
|---|---|
| $TBF = \dfrac{64.719N * W^{0.51456} * H^{0.42246}}{(-0.001A + 0.989)W}$ (8) | $TBF = \dfrac{64.719N * W^{0.51456} * H^{0.42246}}{(-0.003A + 0.9971)W}$ (9) | where
TBF = total body fat as a percentage, N = NIR Response, W = weight in kg, H = height in cm and A = age in years.

Comparison of NIR Empirical Equation Results to NIR Reference Material Results

Figure 4:
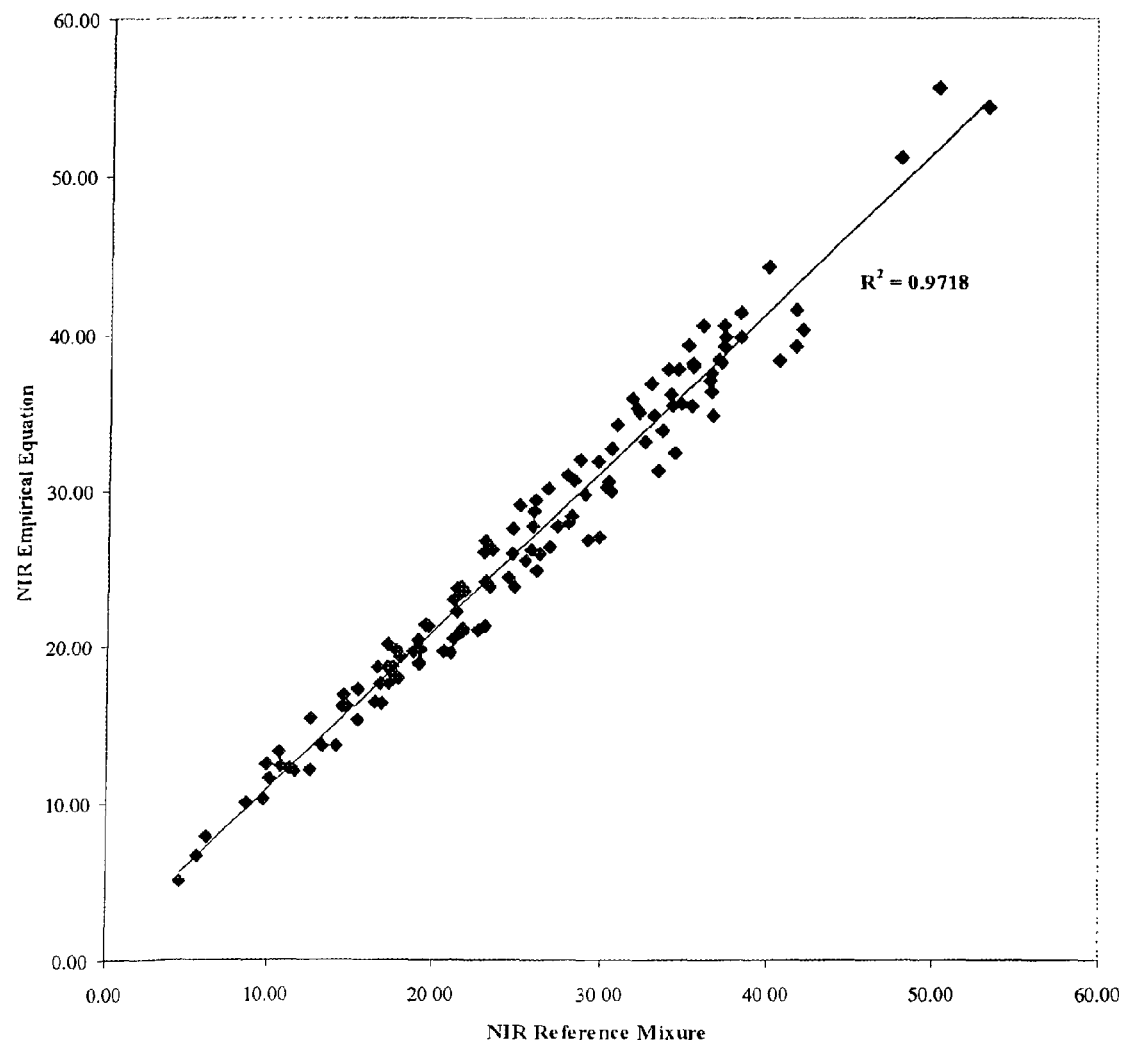
FIG. 4 illustrates the NIR results of reference mixtures and NIR empirical equation for female and male.

A total of 125 volunteers (71 females and 54 males) were scanned and their total body fat content calculated using both the NIR Empirical Equation and the NIR Reference Mixture. FIG. 4 displays the NIR results for females and males combined.

Figure 5:
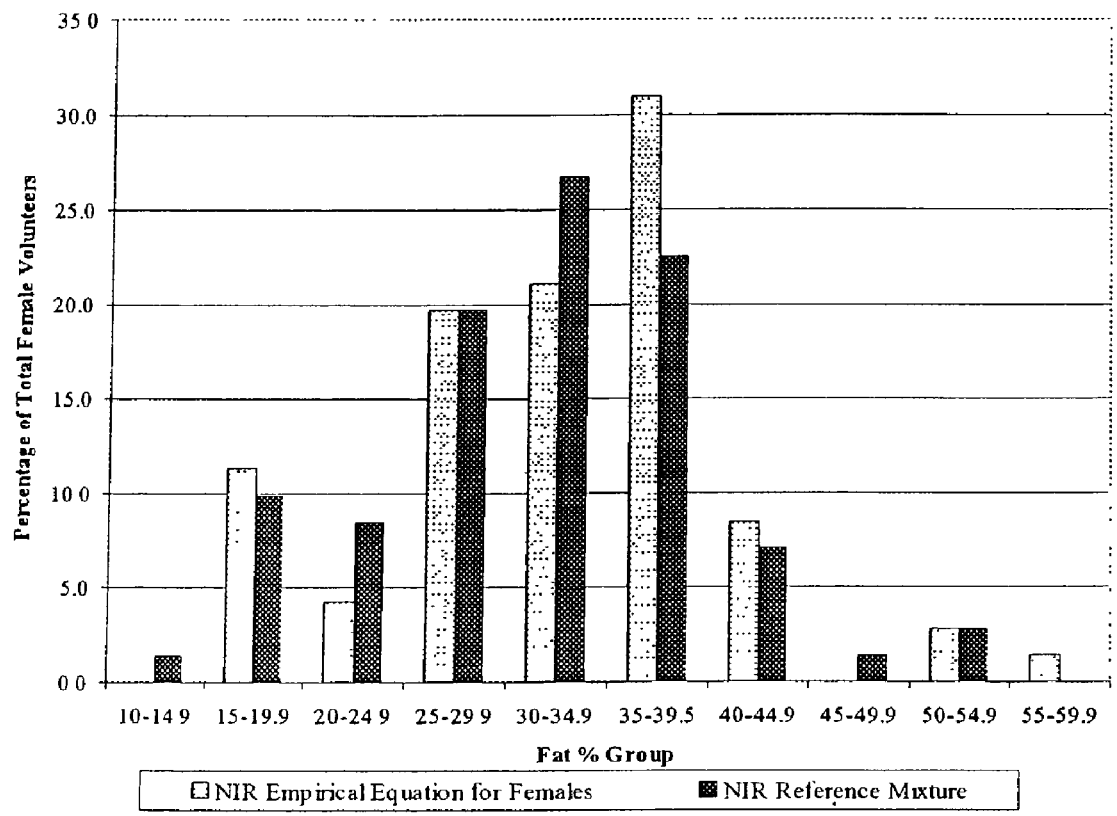
FIG. 5 illustrates a comparison of NIR results for female volunteers and NIR reference samples.
Figure 6:
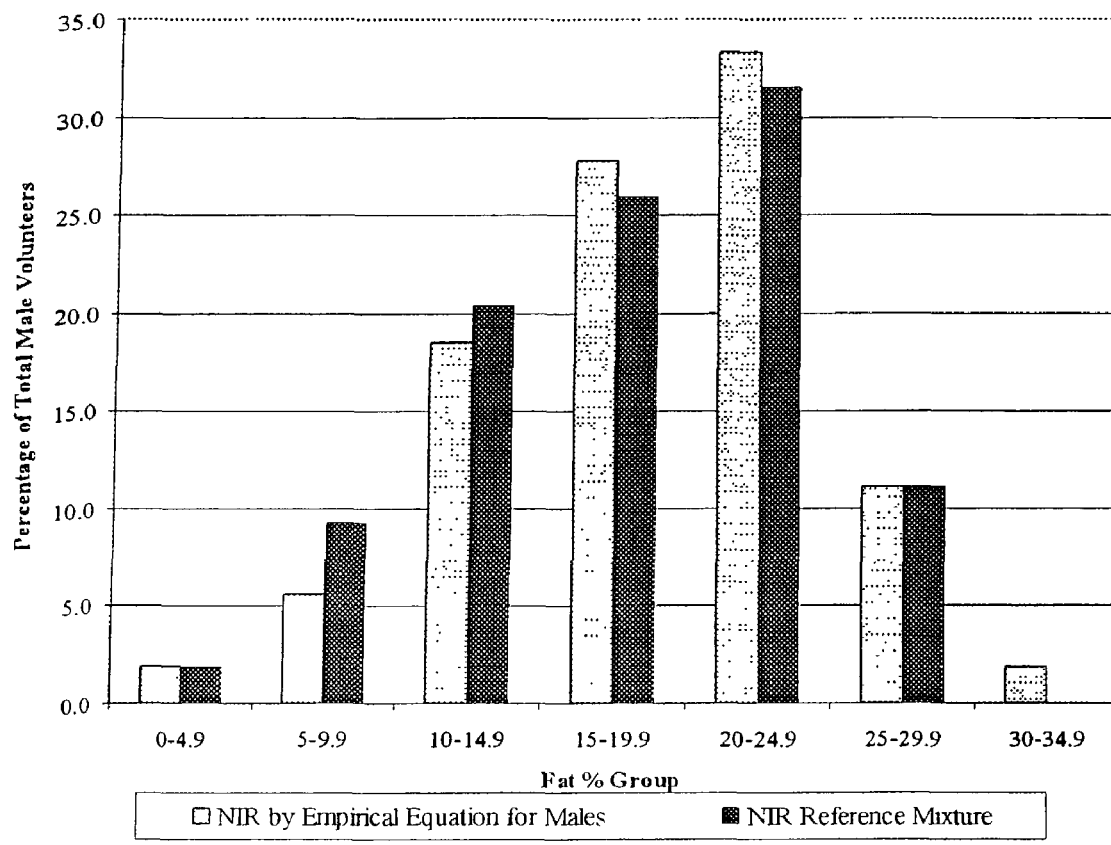
FIG. 6 illustrates a comparison of NIR results for male volunteers and NIR reference samples

FIG. 4 indicates a strong correlation between the NIR Empirical equation and the NIR reference mixture. This relationship is also shown in FIGS. 5 and 6.

Comparison of NIR Results to MRI Results for Volunteers with Similar Gender, Age, Height and Weight The NIR data and MRI data for several volunteers were matched with each other according to gender, age, height and weight. The results are listed below in Table 3. There are 12 groups each with two individuals having similar characteristics. The last two columns in Table 3 show the fat content measured by NIR (equation and reference mixture) and MRI.

TABLE 3

Comparison of NIR and MRI Volunteers.

| Grp | ID No. | Gender | Age | Height (cm) | Weight (kg) | BMI | NIR Resp | MRI SAT (L) | MRI TAT (kg) | % Fat of TotalBody | % Diff. of NIR Relative to MRI | With Ref. Mixture | % Diff. of NIR with Ref. Mixture Relative to MRI |
|---|---|---|---|---|---|---|---|---|---|---|---|---|---|
| 1 | NIR 1006 | Female | 21 | 163 | 67.3 | 25.33 | 0.38 | | | 28.32 | −9.0% | 28.13 | −9.6% |
| | MRI 0163 | Female | 22 | 165.6 | 70.9 | 25.9 | | 23.38 | 22.07 | 31.13 | | | |
| 2 | NIR 1002 | Female | 24 | 165 | 61.4 | 22.54 | 0.46 | | | 36.15 | +13.25% | 34.21 | +7.2% |
| | MIR 0269 | Female | 25 | 169 | 62.7 | 21.9 | | 21.32 | 20.01 | 31.92 | | | |
| 3 | NIR 1060 | Female | 27 | 160 | 68.2 | 26.64 | 0.41 | | | 30.22 | +3.3% | 30.31 | +3.6% |
| | MRI 1184 | Female | 29 | 157.5 | 65 | 26.2 | | 20.12 | 19.02 | 29.26 | | | |
| 4 | NIR 1086 | Female | 34 | 163 | 63 | 23.71 | 0.45 | | | 34.76 | +14.1% | 33.12 | +8.7% |
| | MRI 0218 | Female | 36 | 164 | 63 | 23.4 | | 20.17 | 19.2 | 30.47 | | | |
| 5 | NIR 1078 | Female | 42 | 168 | 73.6 | 26.08 | 0.49 | | | 36.31 | −0.55% | 36.6 | +0.25% |
| | MRI 0329 | Female | 42 | 167.3 | 73.4 | 26.2 | | 27.61 | 26.8 | 36.51 | | | |
| 6 | NIR 1066 | Female | 43 | 170 | 72.3 | 25.02 | 0.37 | | | 27.66 | −12.72% | 27.29 | −13.9% |
| | MRI 0107 | Female | 44 | 170.8 | 72.6 | 24.9 | | 23.79 | 23.01 | 31.69 | | | |
| 7 | NIR 1094 | Female | 44 | 158 | 60.5 | 24.23 | 0.41 | | | 32.67 | −5.6% | 30.54 | −11.7% |
| | MRI 0343 | Female | 45 | 158.6 | 61.6 | 24.5 | | 21.47 | 21.31 | 34.59 | | | |
| 8 | NIR 1034 | Male | 21 | 185 | 88.6 | 25.89 | 0.29 | | | 20.93 | −0.9% | 21.57 | +2.1% |
| | MRI 0201 | Male | 20 | 183.6 | 89.8 | 26.6 | | 19.98 | 18.98 | 21.13 | | | |
| 9 | NIR 1018 | Male | 24 | 170.2 | 63.6 | 21.96 | 0.2 | | | 16.24 | +25% | 14.37 | 10.45% |
| | MRI 0011 | Male | 25 | 172.6 | 64.5 | 21 | | 8.78 | 8.39 | 13.01 | | | |
| 10 | NIR 1031 | Male | 31 | 175 | 77.3 | 25.24 | 0.23 | | | 17.65 | +20.3% | 16.7 | +13.8% |
| | MRI 0315 | Male | 35 | 176.9 | 77.6 | 24.8 | | 11.26 | 11.38 | 14.67 | | | |
| 11 | NIR 1059 | Male | 37 | 180 | 86.4 | 26.67 | 0.24 | | | 18.14 | −4.9% | 17.58 | −7.9% |
| | MRI 0111 | Male | 38 | 181.1 | 88.3 | 26.9 | | 16.78 | 16.85 | 19.08 | | | |
| 12 | NIR 1001 | Male | 49 | 174 | 77.3 | 25.52 | 0.29 | | | 23.66 | +17.07% | 21.29 | +5.3% |
| | MRI 0082 | Male | 49 | 174.3 | 78.1 | 25.7 | | 13.29 | 15.78 | 20.21 | | | |

Figure 7:
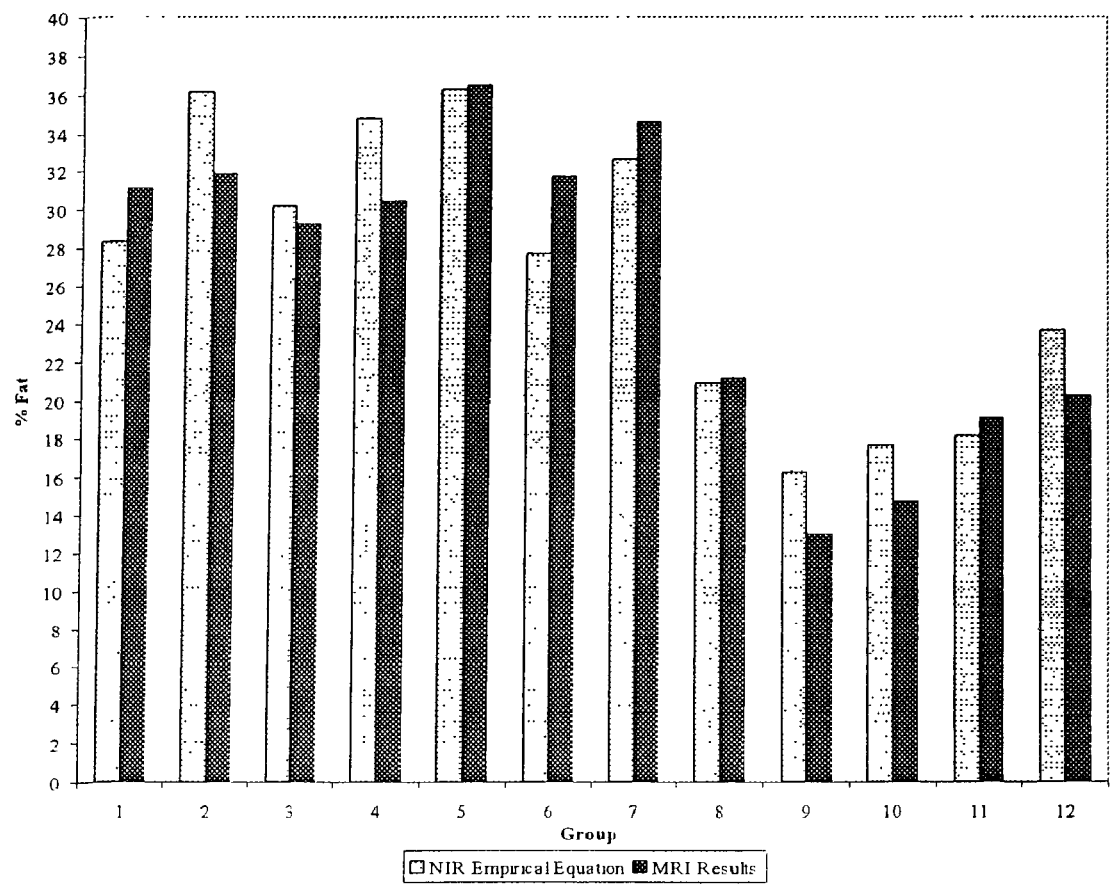
FIG. 7 illustrates a comparison of NIR empirical equation results and MRI results.

The 12 groups of volunteers are displayed in FIG. 7 comparing the MRI results to the NIR Empirical Equation results.

Although the MRI and NIR tests were performed on different volunteers at different times, the correlation between the results of the two techniques is remarkable and the similarities are gender neutral in that there are no obvious differences for the male or female volunteers. The relationship could be further validated by performing both tests on the same individual at the same time and location.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A method for determining the total body fat of a living human organism using an FT-NIR analytical technique, said method comprising the steps of:

(a) directing a beam of light in the near-infrared frequency range from a light source to a subcutaneous layer test site of the body of the living human organism, wherein said beam of light is swept over a pre-determined frequency band of light in the near-infrared frequency range, and wherein said test site is defined by a portion of the body of the living human organism having an epidermis layer, a dermis layer, and said subcutaneous layer, and is subtended by bone or cartilage;

(b) detecting light reflected from said test site of the body of the living human organism by a detector;

(c) recording the intensity of energy absorptions in said reflected light in the form of an interferogram as a function of time;

(d) performing Fourier Transform calculations to the data in said interferogram so as to convert said data in said interferogram to a spectrum;

(e) extracting from said spectrum information concerning specific frequencies and intensity of energy absorptions at said specific frequencies so as to calculate a response value; and (f) determining the total body fat content by incorporating said response value from step (e) into an empirical formula wherein said empirical formula is:

Female:

$$TBF = 64.719 \; N*W^{0.51456}*H^{0.42246}/(-0.001 A + 0.989)W$$

Male:

$$TBF = 64.719 \; N*W^{0.51456}*H^{0.42246}/(-0.003 A + 0.9971)W$$

where TBF is the total body fat in percent, N is said response value, W is the weight in kilograms, H is the height in centimeters, and A is the age in years of the living human organism.

2. The method according to claim 1, further comprising steps:
(g) recording said spectrum by repeating steps (a) to (d) a pre-determined number of times; and
(h) averaging the results from said spectra obtained in step (g) into a spectrum before continuing onto steps (e) and (f).

3. The method according to claim 1, wherein said test site is the back of an ear of the living organism.

4. The method according to claim 1, wherein the calculation of said response value is computer aided.

5. The method according to claim 1, wherein the resolution for at least one of said specific frequencies is between 0.3 nm ($2\ cm^{-1}$ at $8000\ cm^{-1}$) and 2 nm ($13\ cm^{-1}$ at $8000\ cm^{-1}$).

6. The method according to claim 1, wherein the resolution for at least one of said specific frequencies is 1.2 nm ($8\ cm^{-1}$ at $8000\ cm^{-1}$).

7. A method as claimed in claim 1 additionally comprising:
(i) determining a comparative total body fat (TBF) of said living human organism using a comparative MRI analytical technique;
(ii) comparing the comparative TBF content from said MRI analytical technique to the TBF content determined using said FT-NIR analytical technique; and
(iii) validating that the FT-NIR TBF content is within from −12.72% to +25% of the comparative TBF content obtained by said comparative MRI analytical technique.

8. An apparatus for determining the total body fat of a living human organism, said apparatus comprising:
a light source for emitting a beam of light in the near-infrared frequency range, wherein said beam of light is swept over a pre-determined frequency band of light in the near-infrared frequency range;
a delivery means for directing said beam of light from said light source to a subcutaneous layer test site defined by a portion of the body of the living human organism having an epidermis layer, a dermis layer, and said subcutaneous layer, and is subtended by bone or cartilage;
a collecting means for collecting light reflected from said test site;
a detector for detecting said reflected light;
a recorder for recording the intensity of energy absorptions in said reflected light in the form of an interferogram as a function of time;
a computer configured to perform Fourier Transform calculations to the data in said interferogram so as to convert said data in said interferogram to a spectrum and extract from said spectrum information concerning specific frequencies and the intensity of energy absorption at said specific frequencies so as to calculate a response value thereof and then determine the total body fat by incorporating said response value directly into an empirical formula, wherein said empirical formula is Female:
$TBF = 64.719\ N*W^{0.51456}*H^{0.42246}/(-0.001\ A + 0.989)W$
Male:
$TBF = 64.719\ N*W^{0.51456}*H^{0.42246}/(-0.003\ A + 0.9971)W$
where TBF is the total body fat in percent, N is said response value, W is the weight in kilograms, H is the height in centimeters, and A is the age in years of the living human organism.

9. The apparatus according to claim 8, wherein said delivery means is a fibre optic probe.

10. The apparatus according to claim 8, wherein said collecting means is a fibre optic probe.

* * * * *